Уnited States Patent [19]
Godfrey, Jr. et al.

[11] Patent Number: 5,536,833
[45] Date of Patent: Jul. 16, 1996

[54] PROCESS FOR THE PREPARATION OF INTERMEDIATES USEFUL IN THE PREPARATION OF PYRANYL CYANOGUANIDINE DERIVATIVES

[75] Inventors: Jollie D. Godfrey, Jr., Trenton; Richard H. Mueller, Ringoes; Thomas C. Sedergran, Englishtown; Nachimuthu Soundararajan, Kendall Park, all of N.J.

[73] Assignee: E. R. Squibb & Sons, Inc., Princeton, N.J.

[21] Appl. No.: 452,238

[22] Filed: May 26, 1995

Related U.S. Application Data

[60] Division of Ser. No. 128,436, Oct. 1, 1993, Pat. No. 5,463,059, which is a continuation-in-part of Ser. No. 975,498, Nov. 10, 1992, abandoned.

[51] Int. Cl.$^6$ .................. C07D 279/18; C07D 311/74
[52] U.S. Cl. .................. 544/57; 544/62; 544/151; 544/322; 544/376; 546/196; 548/311.4; 548/525; 558/83; 558/411; 549/345; 549/399; 549/404
[58] Field of Search .................. 549/345, 399, 549/404; 546/196; 558/83, 411; 540/542, 553; 548/525, 311.4; 544/57, 62, 151, 322, 376

[56] References Cited

U.S. PATENT DOCUMENTS

| | | | |
|---|---|---|---|
| 4,545,993 | 10/1985 | Okamoto et al. | 514/456 |
| 5,140,031 | 8/1992 | Atwal et al. | 549/345 |

OTHER PUBLICATIONS

P. Barmettler et al., 140.Acid–Catalyzed [3,3]–Sigmatropic Rearrangements of N–Propargylanilines, *Helvetica Chimica Acta*, 1990; 73:1515–1573.

G. F. Hennion et al., The Alkylation of Amines with t–Acetylenic Chlorides. Preparation of Sterically Hindered Amines, *JACS*, 1960;82:4908–4912.

A. Caporusso et al., Copper Catatlyzed Aminolysis of Bromoallenes as a New Efficient Route to Propargylamines, *Tet. Lett.*, 1991;7471–7472.

A. J. Bridges, Phenylthiocopper Trimethylphosphite Complex. A Reagent for the Preparation of Thioallenes, *Tet. Lett.*, 1980;21:4401–4404.

S. C. Joshi et al., A Study Of Claisen Rearrangements Of (1,1–Dimethyl–3–Prop–2–Ynyloxy)–[4H]-1–Benzopyran–4–One Derivatives, *Tet. Lett.*, 1992;48:563–565.

R. D. Murray et al., Synthesis of the Coumarins, Avicennol, Dipetaline and Dipetalolactone, *Tet. Lett.*, 1976;12:953–954.

M. Harfenist et al., The Influence of Structure on the Rate of Thermal Rearrangement of Aryl Propargyl Ethers to the Chromenes. The *gem*–Dimethyl Effect, *J. Org. Chem.*, vol. 37, 1972;6:841–848.

J. M. Evans et al., Synthesis and Antihypertensive Activity of Substituted trans–4–Amino–3,4–dihydro–2, 2–dimethyl–2H–1–benzopyran–3–ols, *J. Med. Chem.*, 1983;26:1582–1589.

F. Bohlmann et al., Synthese von natürlich vorkommenden Hydroxyacetophenon–Derivaten, *Chem. Ber.*, 1972;105:863–873.

S. C. Joshi et al., A Study of Several Claisen Rearrangements, *Tetrahedron*, 1992;48:566–570.

*Primary Examiner*—C. Warren Ivy
*Assistant Examiner*—Amelia Owens
*Attorney, Agent, or Firm*—Ellen K. Park

[57] ABSTRACT

A process for preparing compounds of the formula

I where a, b, c, $R_1$, $R_2$, and $R_3$ are as defined herein including the step of alkylating a phenol of formula

II with an acetylene of formula

III where X is chlorine; bromine; —OC(O)—$R_5$, where $R_5$ is alkyl, aryl or substituted aryl; or —OCO$_2$R$_6$, where $R_6$ is alkyl or in the presence of a catalytic amount of a cuprous or cupric salt. The compounds of formula I are intermediates useful in the preparation of pyranyl cyanoguanidine derivatives.

2 Claims, No Drawings

PROCESS FOR THE PREPARATION OF INTERMEDIATES USEFUL IN THE PREPARATION OF PYRANYL CYANOGUANIDINE DERIVATIVES

REFERENCES TO OTHER APPLICATIONS

This application is a division of U.S. patent application Ser. No. 08/128,436, filed Oct. 1, 1993, now U.S. Pat. No. 5,463,059, which is a continuation-in-part of U.S. patent application Ser. No. 07/975,498, filed Nov. 10, 1992, now abandoned.

FIELD OF THE INVENTION

The present invention relates to novel processes for preparing intermediates useful in preparing compounds having potassium channel activating activity.

BRIEF DESCRIPTION OF THE INVENTION

The present invention is directed to a novel process for preparing compounds of the formula

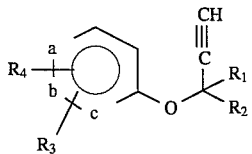

As used in formula I, and throughout the specification, the symbols have the following meanings:

a, b, and c are all carbon atoms or one of a, b and c is a nitrogen atom or —NO— and the others are carbon atoms;

$R_1$ and $R_2$ are each independently hydrogen, alkyl or arylalkyl, or, $R_1$ and $R_2$ taken together with the carbon atom to which they are attached form a 5- to 7-membered carbocyclic ring;

$R_3$ is hydrogen, alkyl, haloalkyl, alkenyl, alkynyl, cycloalkyl, arylalkyl, cycloalkylalkyl, —CN, —NO$_2$, —COR, —COOR, —CONHR, —CONRR', —CF$_3$, S-alkyl, —SOalkyl, —SO$_2$alkyl,

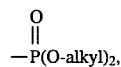

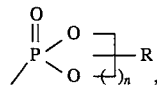

halogen, amino, substituted amino, —OH, —O—alkyl, —OCF$_3$, —OCH$_2$CF$_3$, —OCOalkyl, —OCONRalkyl, —NRCOalkyl, —NRCOOalkyl or —NRCONRR', wherein R and R' are independently hydrogen, alkyl, haloalkyl, aryl, arylalkyl, cycloalkyl, or (cycloalkyl)alkyl;

$R_4$ is hydrogen, alkyl, —OH, —O—alkyl, amino, substituted amino, —NHCOR, —CN, or —NO$_2$; and n is an integer of 1 to 3.

Compounds of formula I may be prepared by alkylating a phenol of formula

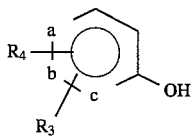

with an acetylene of formula

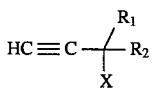

where X is chlorine; bromine; —OC(O)—R$_5$, where R$_5$ is alkyl, aryl or substituted aryl; or —OCO$_2$R$_6$, where R$_6$ is alkyl or

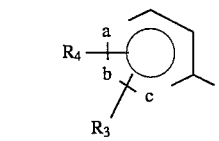

in the presence of a catalytic amount of a cuprous or cupric salt in an organic solvent and a base to form compounds of formula I.

DESCRIPTION OF THE INVENTION

The present invention relates to novel processes for preparing compounds of formula I. Listed below are definitions of various terms used to describe the compounds of the instant invention. These definitions apply to the terms as they are used throughout the specification (unless they are otherwise limited in specific instances) either individually or as part of a larger group.

The term "alkyl" refers to straight and branched chain hydrocarbons, containing 1 to 8 carbons in the normal chain, preferably 1 to 5 carbons such as methyl, ethyl, propyl, isopropyl, butyl, t-butyl, isobutyl, pentyl, 4,4-dimethyl-pentyl, 2,2,4-trimethylpentyl, the various branched chain isomers thereof, and the like as well as such groups including a halo-substituent, such as F, Br, Cl or I such as CCl$_3$ or CF$_3$, an alkoxy substituent, an aryl substituent, an alkyl-aryl substituent, a haloaryl substituent, a cycloalkyl substituent, an alkyl-cycloalkyl substituent, a hydroxy substituent, an alkylamino substituent, an alkanoylamino substituent, an arylcarbonylamino substituent, a nitro substituent, a cyano substituent, a thiol substituent or an alkylthio substituent.

The terms "alkoxy" and "alkylthio" refer to such alkyl groups as described above linked to an oxygen atom or sulfur atom respectively.

The term "alkenyl" refers to such groups as described above for alkyl, further containing at least one carbon to carbon double bond.

The term "alkynyl" refers to such groups as described above for alkyl, further containing at least one carbon to carbon triple bond.

The term "cycloalkyl" as employed herein includes saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl or mono substituted phenyl, 1-naphthyl, 2-naphthyl wherein said substituents is alkyl of 1 to 4 carbons, alkylthio of 1 to 4 carbons, alkoxy of 1 to 4 carbons, halo, nitro, cyano, hydroxy, amino, —NH—alkyl wherein alkyl is of 1 to 4 carbons, —N(alkyl)$_2$ wherein alkyl is of 1 to 4 carbons, —CF$_3$, —OCH$_2$,

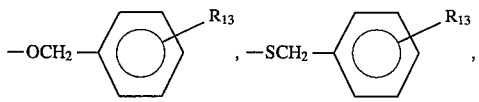

(where R$_{13}$ is hydrogen, alkyl of 1 to 4 carbons, alkoxy of 1 to 4 carbons, alkylthio of 1 to 4 carbons, halo, hydroxy or —CF$_3$), —O—CH$_2$-cycloalkyl, or —S—CH$_2$-cycloalkyl, and all-substituted phenyl, 1-naphthyl, 2-naphthyl wherein said substituents are selected from methyl, methoxy, methylthio, halo, —CF$_3$, nitro, amino, and —OCHF$_2$. Preferred aryl groups include unsubstituted phenyl and monosubstituted or disubstituted phenyl wherein the substituent is nitro, halo, —CF$_3$, alkyl, cyano or methoxy.

The terms "heterocyclo" or "hetero" refer to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6 or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl and 4, 5, 6 or 7-benzofuranzanyl.

The terms "heterocyclo" or "hetero" also include such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH—alkyl wherein alkyl is of 1 to 4 carbons, —N(alkyl)$_2$ wherein alkyl is of 1 to 4 carbons, —CF$_3$, or —OCHF$_2$ or such monocyclic and bicyclic rings wherein two or three available carbons have substituents selected from methyl, methoxy, methylthio, halo, —CF$_3$, nitro, hydroxy, amino and —OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is alkyl, cycloalkyl, aryl, arylalkyl, cycloalkylalkyl or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl- 1-piperazinyl, 4-arylalkyl- 1-piperazinyl, 4-diarylalkyl-1-piperazinyl, 1-pyrrolidinyl, 1-piperidinyl or 1-azepinyl substituted with alkyl, alkoxy, alkylthio, halo, trifluoromethyl or hydroxy.

Compounds of formula I may be prepared by alkylating a phenol of formula

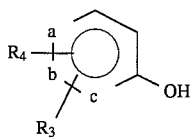 II with an acetylene of formula

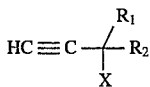 III where X is chlorine; bromine; —OC(O)—R$_5$, where R$_5$ is alkyl, aryl or substituted aryl; or —OCO$_2$R$_6$, where R$_6$ is alkyl or

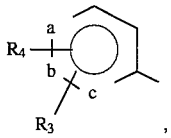

in the presence of a catalytic amount of a cuprous salt (such as cuprous chloride) or a cupric salt (such as cupric acetate monohydrate, cupric bromide, cupric chloride dihydrate, cupric methoxide, cupric trifluoro-methanesulfonate, cupric acetylacetonate, cupric hexafluoroacetylacetonate, cupric tetramethylheptanedionate and cupric trifluoroacetylacetonate) in an organic solvent such as acetonitrile and a base such as 1,8-diazabicyclo-[5.4.0]undec-7-ene (DBU), 1,5-diazabicyclo-[4.3.0]non-5-ene (DBN), or triethylamine, or other trialkylamines to form compounds of formula I.

In preparing compounds of formula I as described above, it may be necessary to protect any amine, hydroxy or thiol groups during the reaction with protecting groups as known in the art.

Compounds of formula II are commercially available or are readily prepared by methods known in the art.

Compounds of formula III may be prepared by methods disclosed in the literature. For example, compounds of formula III where X is chlorine and R$_1$ and R$_2$ are methyl may be prepared as disclosed in G. F. Hennion, et al., *J. Am. Chem. Soc.*, 72, 3542–3545 (1950) and G. F. Hennion et al., *J. Org. Chem.*, 25, 725–727 (1961).

Compounds of formula III where X is bromine and R$_1$ and R$_2$ are methyl may be prepared as disclosed in T. L. Jacobs et at., *J. Org. Chem.*, 28, 1360 (1963). Compounds of formula III where X is —OC(O)—R$_5$, where R$_5$ is alkyl, aryl or substituted aryl, may be prepared as described in G. Hofle et al., *Synthesis*, 619 (1972). Alternatively, compounds of formula III where X is —OC(O)—R$_5$, where R$_5$ is a substituted alkyl such as CCl$_3$ or CF$_3$ may be prepared by treating compounds of formula IIIa

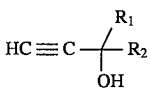

with trichloroacetyl chloride, trifluoroacetic anhydride or trichloroacetic anhydride in the presence of a base such as triethylamine or DBU. Compounds of formula IIIa are either commercially available or known in the art.

Compounds of formula III where X is —OCO$_2$R$_6$, where R$_6$ is alkyl or

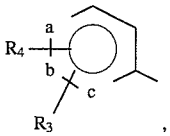

may be prepared as disclosed in J. Tsuji et at., *J. Organometallic Chemistry*, 417, 305–311 (1991) and U.S. Pat. No.

3,348,939 to Delta W. Gier. The above cited references are incorporated by reference herein.

Preferred compounds of formula III are those where X is chlorine; —OC(O)—$R_5$, where $R_5$ is substituted alkyl, most preferably trifluoromethyl; or —$OCO_2R_6$, where $R_6$ is methyl or ethyl.

It is also within the scope of this invention that compounds of formula III where X is trifluoroacetate or trichloroacetate may be formed in situ and reacted with compounds of formula II to produce the compounds of formula I.

Compounds of formula I are key intermediates in the preparation of pyranyl cyanoguanidine derivatives of the formula

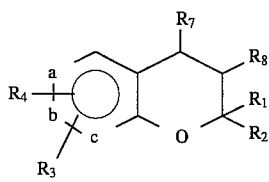  IV were a, b, c, $R_1$, $R_2$, $R_3$, and $R_4$ are as defined for formula I and $R_7$ is

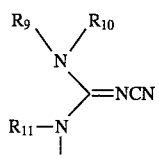

or

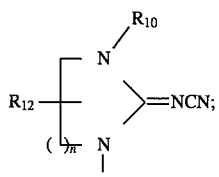

$R_8$ is hydrogen, hydroxy, or —OC(O)—$CH_3$;

$R_9$ and $R_{10}$ are independently hydrogen, alkyl, alkenyl, aryl, (heterocyclo)alkyl, heterocyclo, arylalkyl, cycloalkyl, (cycloalkyl)alkyl or substituted alkyl; or these groups optionally substituted with alkoxy, alkylthio or substituted amino; or $R_9$ and $R_{10}$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl-1-piperazinyl or 4-arylalkyl- 1-piperazinyl, wherein each of the so-formed groups are optionally substituted with alkyl, alkoxy, alkylthio, halogen or trifluoromethyl; and $R_{11}$ and $R_{12}$ are independently hydrogen, alkyl, alkenyl, aryl, arylalkyl, cycloalkyl or cycloalkylalkyl; or $R_{11}$ is as defined above and $R_{12}$ is an aryl group fused to 2 carbon atoms of the cyanoguanidine ring portion.

Compounds of formula IV and methods of preparing such compounds are disclosed in U.S. Pat. No. 5,140,031, the disclosure of which is incorporated by reference herein.

Preferred compounds of formula IV are those where $R_7$ is

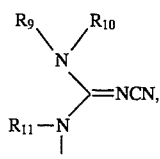

and $R_9$ is mono- or di-substituted phenyl.

An exemplary method of preparing the compounds of formula IV where $R_7$ is

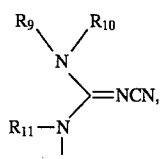

using the intermediates of formula I, prepared as disclosed herein includes cyclizing compounds of formula I utilizing heat as known in the art to form compounds of formula

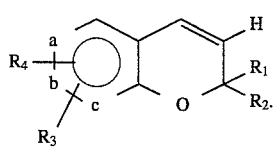  V

Compounds of formula V are then convened to compounds of formula

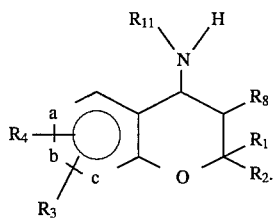  VI

Compounds of formula VI are then reacted with a thiourea of formula

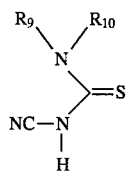  VII to obtain the compounds of formula IV where $R_7$ is

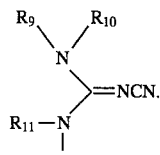

Other compounds of formula IV may be prepared as disclosed in U.S. Pat. No. 5,140,301.

The thiourea of formula VII, wherein $R_{10}$ is hydrogen can be prepared by heating an isothiocyanate of the formula VIII $R_9N=C=S$ with either monosodium cyanamide or with cyanamide in the presence of an organic base, such as triethylamine.

The other thioureas of formula VII can be prepared by standard methods described in the literature, such as by C. R. Rasmussen, et al., *Synthesis*, p. 456 (1988); and V. V. Mozolis et al., *Russian Chemical Reviews*, 42, 587 (1973).

The following examples and preparations describe the manner and process of making and using the preferred embodiments of the invention and are illustrative rather than limiting. It should be understood that there may be other embodiments which fall within the spirit and scope of the invention as defined by the claims appended hereto.

Example 1

4-[(1,1-Dimethyl-2-propynyl)oxy]benzonitrile

A solution of cuprous chloride in acetonitrile was prepared immediately before use. In a 10 mL volumetric flask was placed cuprous chloride (25.56 mg, 0.2582 mmol) and 10 mL of anhydrous acetonitrile.

To a solution of 4-cyanophenol (9.0 g, 75.55 mmol, commercially available) and anhydrous acetonitrile (120 mL) at ~0° C. under argon was added 1,8-diazabicyclo-[5.4.0]undec-7-ene (DBU, 14.0 mL, 93.61 mmol, 1.24 eq based on the input of 4-cyanophenol). A temperature increase to 12.6° C. was observed. After the solution had cooled to 0° C., copper bronze (cooper powder, 49.8 mg, 0.783 mmol, 0.0104 eq, 1.04 mol %) was added followed by the addition of a portion of the cuprous chloride in acetonitrile solution prepared above (600 μL, 15.49 μmole, 0.000205 eq., 0.0205 mol %). To the resulting mixture was added, dropwise over 12 minutes, 3-chloro-3-methyl-1-butyne (7.03 g, 68.54 mmol, 0.907 eq. based on the input of 4-cyanophenol). The resulting mixture was allowed to stir at 0° C. under argon. After stirring for 10 hours, the reaction mixture was filtered through a small pad of Celite (to remove the remaining copper bronze) using additional acetonitrile to complete the transfer and to wash the filter bed. The filtrate was concentrated at reduced pressure (bath temperature 40° C.) and the residue was partitioned between 1N HCl (100 mL) and toluene (400 mL). The organic fraction was washed with 1N HCl ( 2×60 mL), 1N NaOH (2×60 mL), and brine. After drying (magnesium sulfate), the solvent was removed at reduced pressure to give crude title compound as a pale yellow oil (10.68 g). Distillation of the crude material (bulb-to-bulb, ~70°–90° C., ~0.15 mm Hg) afforded the title compound as a colorless, low melting (mp 28°–29° C.) solid (10.40 g).

Elemental Analysis for $C_{12}H_{11}NO$:

Calcd: C, 77.81; H, 5.99; N, 7.56;

Found: C, 77.76; H, 6.02; N, 7.41.

Example 2

4-[(1,1-Dimethyl-2-propynyl)oxy]benzonitrile

To a solution of 4-cyanophenol (655 g, 5.50 mol) in acetonitrile (10 L) at 0° C. under nitrogen was added cuprous chloride (495 mg, 5 mmol, 0.001 eq., 0.1 mol %). DBU (970 mL 6.51 mol) was added slowly while maintaining the temperature at <5° C. 3-Chloro-3-methyl-1-butyne (570 mL, 5 mole) was added. After stirring for 4 hours at 0° C., the mixture was concentrated at reduced pressure and the residue was partitioned between ethyl acetate (5 L) and 1N HCl ( 2 L). The organic fraction was washed with 1N NaOH (2×1 L), water (1 L), and brine (1 L). After drying (magnesium sulfate), the solvent was removed at reduced pressure to afford the title compound as a yellow oil (930 g) which was used without further purification.

Example 3

4-[(1,1-Dimethyl-2-propynyl)oxy]benzonitrile

To a solution of 4-cyanophenol (3.0 g, 25.18 mmol) and methyl 1,1-dimethyl-2-propynyl carbonate (3.93 g, 27.64 mmol) in acetonitrile (24 mL) at 0° C. under argon was added DBU (5.0 mL, 33.43 mmol). To the resulting solution at 0° C. was added cuprous chloride (7.47 mg, 0.003 eq., 0.3 mol %) and copper bronze (83 mg). After stirring at 0° C. for 23 hours, the reaction mixture was filtered and the filtrate was diluted with toluene (~400 mL). The resulting solution was washed with 1N HCl (×2), 1N NaOH (×2), and brine. After drying (magnesium sulfate), the solvent was removed at reduced pressure to give crude title compound as a pale yellow oil (4.18 g). Distillation of the crude material (bulb-to-bulb) afforded the title compound as a colorless, low melting (mp 28°–29° C.) solid (4.02 g).

Example 4

Trichloroacetic acid 1,1 dimethyl 2-propynyl ester

2-Methyl-3-butyn-2-ol was added to n-butyllithium in THF at −30° C. and the mixture gradually warmed to 5° C. After stirring 5 minutes, the mixture was recooled to −30° C. and trichloroacetyl chloride was added. At 5° C., a precipitate began to form. The reaction was stirred for 5 hours and checked by NMR. The alcohol was consumed. Hexane was added to the mixture and the salts removed by filtration to give a clear solution. The solvents were removed under vacuum to give a clear slightly yellow oil. The yield was 66.0% and analysis (gas chromatography) indicated a homogeneity index of 86%.

Alternate Procedures 1. 4-Dimethylamino pyridine (DMAP)/triethylamine was used in place of n-butyllithium in the above procedure. Trichloroacetyl chloride was added to the 2-methyl-3-butyn-2-ol, triethylamine and DMAP at 0° to 5° C. After warming to 22° C., the reaction was 66% complete. Stirring for an additional hour did not increase the conversion. Therefore, 0.5 eq. of triethylamine and trichloroacetyl chloride were added and stirred for 16 hours. The 2-methyl-3-butyn-2-ol was entirely consumed. The reaction mixture was diluted with hexane and washed with water, 1N HCl, saturated sodium bicarbonate and brine. After drying over anhydrous magnesium sulfate, the solvent was removed under vacuum. The yield was 75.5% and analysis (gas chromatography) indicated a homogeneity index of 94%.

2. The above alternative reaction was run at twice the concentration and with an additional 0.5 eq. of triethylamine and trichloroacetyl chloride. The reaction was complete after 1 hour at 0° to 5° C. as indicated by the absence of 2-methyl-3-butyn-2-ol by GC analysis. After stirring the reaction at 22° C. for 2.5 days, the GCHI of the product was unchanged. The reaction was worked up as described above and 60.4 g of product was isolated in a 87.8% yield and analysis (gas chromatography) indicated a homogeneity index of 88%.

Example 5

4-[(1,1-Dimethyl-2-propynyl)oxy]benzonitrile

2-Methyl-3-butyn-2-ol (56.4 mL, 0.58 mol) was dissolved in acetonitrile (300 mL) and was cooled to 0° C. under nitrogen. DBU (112 mL, 0.75 mol) was then added over a period of 15 minutes with the temperature not exceeding 0° C. After stirring 5 minutes, trifluoroacetic anhydride (82.0 mL, 0.58 mol) was added slowly during a 45 minute period while maintaining the temperature at less than 2° C.

4-Hydroxybenzonitrile (60.0 g, 0.50 mol) and cuprous chloride (0.05 g, 0.1 mol %) were dissolved in acetonitrile (300 mL) at 22° C. This solution was then cooled to 0° C. under nitrogen. DBU (97.1 mL, 0.65 mol) was added over a period of 15 minutes between 0° and 5° C.

The preformed 2-methyl-3-butyn-2-ol ester solution was dripped into the 4-hydroxybenzonitrile solution over 3 hours, keeping the temperature between −2° C. and 0° C. After stirring 2 additional hours, the acetonitrile was removed under vacuum. The residue was dissolved in ethyl acetate (750 mL) and washed with 1N sodium hydroxide (3×300 mL portions), 1N hydrochloric acid (3×300 mL portions), water (1×300 mL portion), and brine (1×300 mL). The organic layer was then dried over anhydrous magnesium sulfate and the solvent evaporated under reduced pressure yielding the title compound (82.9 g) as a low melting solid. Analysis (HPLC:high performance liquid chromatography) indicated a homogeneity index of 97%.

Example 6

4-[(1,1-Dimethyl-2-propynyl)oxy]benzonitrile

To a solution of 4-cyanophenol (6.55 g, 55.0 mmol) in anhydrous acetonitrile (50 mL) at ~0° C. under argon was added DBU (9.04 mL, 60.45 mmol). After the solution had cooled to ~0° C., 3-chloro-3-methyl-1-butyne (5.13 g, 50 mmol) was added followed by cupric chloride dihydrate (9.62 mg, 0.056 mmol). After stirring at ~0° C. for 5 hours, the mixture was concentrated at reduced pressure. The residue was partitioned between 1N HCl (50 mL) and toluene (300 mL). The organic fraction was washed with 1N HCl (2×50 mL), 1N NaOH (2×50 mL), and brine. After drying (magnesium sulfate), the solvent was removed at reduced pressure to give crude title compound as a nearly colorless oil. Distillation of the crude material (bulb to bulb) afforded the title compound as a colorless, low melting solid (7.25 g).

Example 7

4-[(1,1-Dimethyl-2-pronynyl)oxy]benzonitrile

To a solution of 4-cyanophenol (6.55 g, 55.0 mmol) in anhydrous acetonitrile (50 mL) at ~0° C. under argon was added DBU (9.90 mL, 6.2 mmol). After the solution had cooled to ~0° C., 3-chloro-3-methyl-1-butyne (7.10 g, 69.2 mmol) was added followed by copper(II) acetylacetonate (87.4 mg, 0.33 mmol). After stirring at ~0° C. for 7 hours, the mixture was concentrated at reduced pressure. The residue was partitioned between 1N HCl (70 mL) and toluene (300 mL). The organic fraction was washed with 1N HCl (2×60 mL), 1N NaOH (2×50 mL), 1N NaHCO$_3$, and brine. After drying (magnesium sulfate), the solvent was removed at reduced pressure to give crude title compound as a pale yellow oil. Distillation of the crude material (bulb to bulb) afforded the title compound as a colorless, low melting solid (9.56 g).

Example 8

4-[(1,1-Dimethyl-2-propynyl)oxy]benzonitrile

To a solution of 4-cyanophenol (3.0 g, 25.18 mmol) and methyl 1,1-dimethyl-2-propynyl carbonate (3.93 g, 27.64 mmol) in anhydrous acetonitrile (24 mL) at 0° C. under argon was added DBU (5.0 mL, 33.43 mmol). After the solution had cooled to ~0° C., cupric chloride dihydrate (14.6 mg, 0.086 mmol) was added. After stirring at ~0° C. for 23 hours, the mixture was concentrated at reduced pressure. The residue was partitioned between 1N HCl (44 mL) and toluene (200 mL). The organic fraction was washed with 1N HCl (2×40 mL), 1N NaOH (2×40 mL), 1N NaHCO$_3$, and brine. After drying (magnesium sulfate), the solvent was removed at reduced pressure to give crude title compound as a pale yellow oil. Distillation of the crude material (bulb to bulb) afforded the title compound as a colorless, low melting solid (4.05 g).

Example 9

4-[(1,1-Dimethyl-2-propynyl)oxy]benzonitrile

To a solution of 4-cyanophenol (3.0 g, 25.18 mmol) and methyl 1,1-dimethyl-2-propynyl carbonate (3.93 g, 27.64 mmol) in anhydrous acetonitrile (24 mL) at 0° C. under argon was added DBU (5.0 mL, 33.43 mmol). After the solution had cooled to ~0° C., copper(II) acetylacetonate (66.4 mg, 0.254 mmol) was added. After stirring at ~0° C. for 72 hours. the mixture was concentrated at reduced pressure. The residue was partitioned between 1N HCl (40 mL) and toluene (200 mL). The organic fraction was washed with 1N HCl (2×40 mL), 1N NaOH (2×40 mL), 1N NaHCO$_3$, and brine. After drying (magnesium sulfate), the solvent was removed at reduced pressure to give crude title compound as a pale yellow oil. Distillation of the crude material (bulb to bulb) afforded the title compound as a colorless, low melting solid (4.59 g).

Example 10

4-[(1,1-Dimethyl-2-propynyl)oxy]benzonitrile

To a solution of 2-methyl-3-butyn-2-ol (4.88 g, 58.0 mmol) in anhydrous acetonitrile (30 mL) under argon and cooled in an ice-salt bath (–5° C.) was added DBU (11.2 mL, 74.9 mmol). Trifluoroacetic anhydride (8.2 mL, 58.0 mmol) was added during a 25 minute period while maintaining the temperature at less than 2° C. The resulting 1,1-dimethyl-2propynyl trifluoroacetate solution was allowed to stir at ~0° C. (ice bath) for 30 minutes before addition to the 4-cyanophenol solution.

To a solution of 4-cyanophenol (6.0 g, 50.4 mmol) in anhydrous acetonitrile (30 mL) under argon and cooled in an ice-salt bath (–4° C.) was added DBU (9.7 mL, 64.9 mmol) and cupric chloride dihydrate (9.3 mg, 0.055 mmol).

The 1,1-dimethyl-2-propynyl trifluoroacetate solution, maintained at 0° C., was added to the 4-cyanophenol solution over a 40 minute period while keeping the temperature at ~0° C. The resulting mixture was stirred at ~0° C. (ice bath). After stirring for 5 hours, the mixture was concentrated at reduced pressure. The residue was partitioned between water (50 mL) and toluene (300 mL). The organic fraction was washed with 1N HCl (3×50 mL), 1N NaOH (2×50 mL), 1N NaHCO₃, and brine. After drying (magnesium sulfate), the solvent was removed at reduced pressure to give crude title compound as a very pale yellow oil. Distillation of the crude material (bulb to bulb) afforded the title compound as a colorless, low melting solid (8.04 g).

Example 11

4-[(1,1-Dimethyl-2-propynyl)oxy]benzonitrile

To a solution of 2-methyl-3-butyn-2-ol ( 5.85 g, 69.5 mmol) in anhydrous acetonitrile (36 mL) under argon and cooled in an ice-salt bath (–5° C.) was added DBU (13.5 mL, 90.3 mmol). Trifluoroacetic anhydride (9.8 mL, 69.4 mmol) was added during a 33 minute period while maintaining the temperature at less than 2° C. The resulting 1,1-dimethyl-2propynyl trifluoroacetate solution was allowed to stir at ~0° C. (ice bath) for 30 minutes before addition to the 4-cyanophenol solution.

To a solution of 4-cyanophenol (6.0 g, 50.4 mmol) in anhydrous acetonitrile (30 mL) under argon and cooled in an ice-salt bath (–3° C.) was added DBU (9.7 mL, 64.9 mmol) and copper(II) acetylacetonate (78 mg, 0.298 mmol).

The 1,1-dimethyl-2-propynyl trifluoroacetate solution, maintained at 0° C., was added to the 4-cyanophenol solution over a 35 minute period while keeping the temperature at ~0 ° C. The resulting mixture was stirred at ~0° C. (ice bath). After stirring for 90 minutes, water (10 mL) was added and the resulting mixture was concentrated at reduced pressure. The residue was partitioned between water (50 mL) and toluene (300 mL). The organic fraction was washed with 1N HCl (3×50 mL), 1N NaOH (2×50 mL), 1N NaHCO₃, and brine. After drying (magnesium sulfate), the solvent was removed at reduced pressure to give crude title compound as a yellow oil. Distillation of the crude material (bulb to bulb) afforded the title compound as a colorless, low melting solid (8.93 g).

What is claimed is:

1. A process for the preparation of compounds of formula

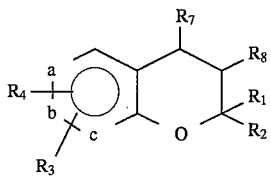

IV where a, b, and c are all carbon atoms or one of a, b and c is a nitrogen atom or —NO— and the others are carbon atoms;

$R_1$ and $R_2$ are each independently hydrogen, alkyl or arylalkyl, or, $R_1$ and $R_2$ taken together with the carbon atom to which they are attached form a 5- to 7-membered carbocyclic ring;

$R_3$ is hydrogen, alkyl, haloalkyl, alkenyl, alkynyl, cycloalkyl, arylalkyl, cycloalkylalkyl, —CN, —NO₂, —COR, —COOR, —CONHR, —CONRR', —CF₃, S-alkyl, —SOalkyl, —SO₂alkyl,

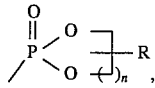

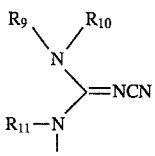

halogen, amino, substituted amino, —OH, —O—alkyl, —OCF₃, —OCH₂ CF₃, —OCOalkyl, —OCONRalkyl, —NRCOalkyl, —NRCOOalkyl or —NRCONRR', wherein R and R' are independently hydrogen, alkyl, haloalkyl, aryl, arylalkyl, cycloalkyl, or (cycloalkyl)alkyl;

$R_4$ is hydrogen, alkyl, —OH, —O—alkyl, amino, substituted amino, —NHCOR, —CN, or —NO₂;

$R_7$ is

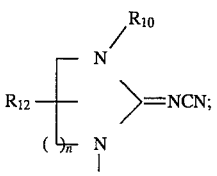

$R_8$ is hydrogen, hydroxy, or —OC(O)—CH₃;

$R_9$ and $R_{10}$ are independently hydrogen, alkyl, alkenyl, aryl, (heterocyclo)alkyl, heterocyclo, arylalkyl, cycloalkyl, (cycloalkyl)alkyl or substituted alkyl; or these groups optionally substituted with alkoxy, alkylthio or substituted amino; or $R_9$ and $R_{10}$ taken together with the nitrogen atom to which they are attached form 1-pyrrolidinyl, 1-piperidinyl, 1-azepinyl, 4-morpholinyl, 4-thiamorphilinyl, 1-piperazinyl, 4-alkyl- 1-piperazinyl or 4-arylalkyl-1-piperazinyl, wherein each of the so-formed groups are optionally substituted with alkyl, alkoxy, alkylthio, halogen or trifluoromethyl; and $R_{11}$ and $R_{12}$ are independently hydrogen, alkyl, alkenyl, aryl, arylalkyl, cycloalkyl or cycloalkylalkyl; or $R_{11}$ is as defined above and $R_{12}$ is an aryl group fused to 2 carbon atoms of the cyanoguanidine ring portion; and n is an integer of 1 to 3; comprising the steps of (A) preparing a compound of the formula I

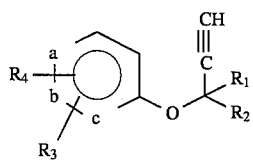

comprising the step of alkylating a phenol of formula

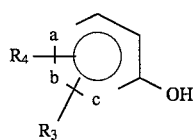        II with an acetylene of formula

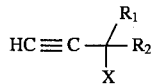        III where X is chlorine; bromine; —OC(O)—$R_5$, where $R_5$ is alkyl, aryl or substituted aryl; or —OCO$_2$$R_6$, where $R_6$ is alkyl or

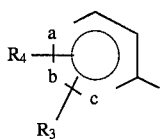

in the presence of a catalytic amount of a cuprous or cupric salt; and (B) converting said compound of the formula I prepared in step (A) to said compound of formula IV.

2. The process as recited in claim 1 wherein a compound of the formula

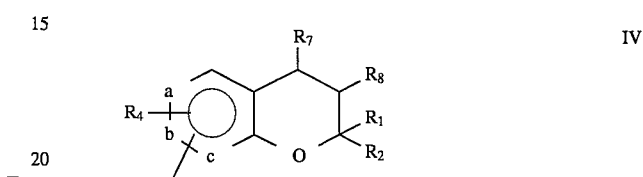        IV where $R_7$ is

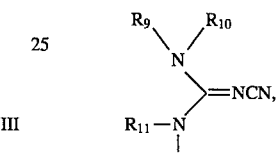

and $R_9$ is mono- or di-substituted phenyl is prepared.

* * * * *